United States Patent
Forsyth et al.

(10) Patent No.: US 6,541,421 B1
(45) Date of Patent: Apr. 1, 2003

(54) BUFFERED PHOSPHORUS CONTAINING SOLUTION

(75) Inventors: Alastair James Forsyth, Portion 36, Farm Rietvallei 180 IQ, District Krugersdorp, 1739 (ZA); Tomasz Antoni Modro, Pretoria (ZA)

(73) Assignee: Alastair James Forsyth, Krugersdorp (ZA)

( * ) Notice: Subject to any disclaimer, the term of this patent is extended or adjusted under 35 U.S.C. 154(b) by 1 day.

(21) Appl. No.: 09/679,118

(22) Filed: Oct. 4, 2000

(30) Foreign Application Priority Data

Dec. 10, 1999 (ZA) ................................................ 99/7596

(51) Int. Cl.$^7$ ........................ A01N 59/26; A01N 43/50; C05B 17/00; C05B 21/00; C05B 9/00
(52) U.S. Cl. ........................ 504/101; 424/600; 424/601; 424/602; 424/604; 424/605; 424/606; 424/666; 424/688; 424/690; 424/692; 424/693; 424/715; 424/716; 424/717; 514/396; 71/32; 71/48; 71/49
(58) Field of Search ................................ 71/32, 48, 49; 504/101; 424/600–602, 604–606, 666, 688, 690, 692, 693, 715–717; 514/396

(56) References Cited

U.S. PATENT DOCUMENTS

| | | | |
|---|---|---|---|
| 4,075,324 A | 2/1978 | Thizy et al. ................ | 424/128 |
| 4,251,255 A | 2/1981 | Wagner et al. ................ | 71/27 |
| 5,514,200 A | 5/1996 | Lovatt ............................. | 71/11 |
| 5,800,837 A | 9/1998 | Taylor ........................ | 424/601 |
| 5,830,255 A | * 11/1998 | Lovatt ............................. | 71/11 |
| 5,830,255 A | * 11/1998 | Lovatt ............................. | 71/11 |
| 5,925,383 A | 7/1999 | Taylor ........................ | 424/601 |
| 6,113,665 A | 9/2000 | Lovatt ............................. | 71/11 |

FOREIGN PATENT DOCUMENTS

| | | |
|---|---|---|
| AU | 6396086 | 4/1987 |
| CA | 1 250 445 | 2/1989 |
| JP | WO 98/48628 | 11/1998 |

* cited by examiner

*Primary Examiner*—John Pak
(74) *Attorney, Agent, or Firm*—Fish & Richardson P.C.

(57) ABSTRACT

This invention relates to a buffered phosphorus containing solution comprising at least one phosphorus compound selected from the group consisting of phosphorous acid, hypophosphorous acid, polyphosphorous acid polyhypophosphorous acid, and salts thereof. The solution also contains a buffer including an organic base in the form of a nitrogen containing compound and its conjugate acid. The solution may be used as a fertilizer or as a fungicide. The invention also relates to a method of preparing such a solution.

19 Claims, No Drawings

BUFFERED PHOSPHORUS CONTAINING SOLUTION

TECHNICAL FIELD

This invention relates to buffered phosphorus containing solutions, including such fertiliser solutions and including such fungicidal solutions.

BACKGROUND ART

The use of phosphorous acid and phosphites instead of phosphoric acid and phosphates as fertilisers and/or fungicides are known. Phosphorous acid and phosphites have the advantage over phosphates in that they are more readily absorbable by the foliage of plants such as citrus and avocado plants. Another advantage is that phosphites have fungicidal properties in addition to their fertilising properties.

Accordingly phosphite compositions in an unbuffered form have been marketed for foliage uptake and for applications to the soil. These compositions are sold as concentrated solutions that have to be diluted with water prior to application. It will be appreciated that the pH of the water used during dilution will have an influence on the pH of the diluted solution. In some cases the quality of the water may be such that the pH of the diluted solution may be influenced to such an extent that it falls outside the range where the diluted solution is suitable to be taken up by foliage. The pH range, which is acceptable for the solution to be taken up by the plant foliage, differs from one plant type to another, but usually it is from a pH of about 5 to a pH of about 7.

U.S. Pat. No. 4,075,324 describes fungicidal compositions containing phosphorous acid, inorganic and organic salts thereof.

U.S. Pat. No. 5,514,200 describes a buffered fertiliser composition comprising an organic acid and salts thereof and a phosphorous containing acid and salts thereof, which upon dilution forms a substantially fully solubilised fertiliser having a foliage acceptable pH for phosphorous uptake. The patent accordingly teaches how to overcome the above disadvantage. The patent teaches that the fertiliser comprises a double or multiple buffer systems that stabilise the phosphorous species against oxidation to phosphate. It further claims that the properties of phosphite that make it desirable as a fertiliser are enhanced when formulated as a double or multiple buffer according to the invention. Furthermore it is claimed that increased solubility of the formulation is obtained and that greater uptake of phosphorous is achieved.

It is an object of the present invention to provide an alternative buffered phosphorus containing solution, especially to such solutions for application to plants.

DISCLOSURE OF THE INVENTION

According to the present invention there is provided a buffered phosphorus containing solution containing at least one phosphorus compound selected from the group consisting of phosphorous acid, hypophosphorous acid, polyphosphorous acid, polyhypophosphorous acid, and salts thereof; and a buffer including an organic base in the form of a nitrogen containing compound and is conjugate acid.

It will be appreciated that since the phosphorus containing solution is in fact a solution the phosphorus compound will usually be dissolved therein.

Preferably the solution comprises an aqueous solution.

The solution may comprise a concentrated solution of the phosphorus compound. Preferably the solution has a concentration from 2 $mol.dm^{-3}$ to 8 $mol.dm^{-3}$ of the phosphorus compound More preferably the concentration is from 4.5 $mol.dm^{-3}$ to 7.5 $mol.dm^{-3}$. Most preferably the concentration is about 6.8 $mol.dm^{-3}$.

The phosphorus compound preferably comprises phosphorous acid and/or a salt thereof. Most preferably it comprises a salt of phosphorous acid. Preferably it comprises an alkali metal salt or an alkaline earth metal salt of phosphorous acid. Most preferably it comprises a potassium salt of phosphorous acid.

The salt of the phosphorous acid may comprise a monosubstituted and/or disubstituted phosphorous acid. Preferably it comprises a mixture of mono-and disubstituted phosphorous acid. Preferably it comprises a mixture of $KH_2PO_3$ and $K_2HPO_3$. Preferably the monosubstituted phosphorous acid is present in a larger molar amount than the disubstituted phosphorous acid. Preferably the molar ratio between the mono and disubstituted phosphorous acid is from 4:1 to 3:1. Preferably it is about 3.3:1.

The salt of phosphorous acid may be prepared by reacting phosphorous acid with a suitable base. Preferably the base is added in such an amount to provide the solution at a pH suitable for foliar uptake. Usually this is at a pH from about 5 to about 7. Preferably the pH is from about 6 to 7. Most preferably the pH is about 6.5.

The salt may be prepared by first reacting phosphorous acid with a first base (such as potassium carbonate) and thereafter reacting it with another base (such as KOH). The first base may comprise a compound which does not include hydroxide, preferably it is a carbonate, and preferably it is an alkali metal carbonate. The other base may comprise a hydroxide containing compound, preferably an alkali metal hydroxide. The first base may be a weaker base than the second base. It is believed that the addition of a salt such as potassium carbonate increases the solubility of the phosphorous acid salt. By using potassium carbonate to first react with phosphorous acid, a solubility of 550 g/l phosphorous acid was obtained which is much higher than previous obtained concentrations.

The buffer may be prepared by mixing the organic base in the form of the nitrogen containing compound with an inorganic acid, preferably a mineral acid.

The nitrogen containing compound may comprise a heterocyclic compound containing at least one nitrogen atom as a ring member, preferably two nitrogen atoms as ring members. The ring may comprise from 5 to 6 members, but preferably it comprises 5 members. Preferably the heterocyclic compound is aromatic. In a most preferred embodiment of the invention the heterocyclic compound comprises imidazole.

The mineral acid may comprise hydrochloric acid, sulphuric acid or nitric acid Preferably it comprises hydrochloric acid.

The buffer preferably buffers the solution at a pH suitable for foliar uptake. Usually this is at a pH from about 5 to about 7. Preferably the pH is from about 6 to 7. Most preferably it is about 6.5.

The buffer comprising imidazole and its salt formed with hydrochloric add is a very effective buffer and relatively small amounts of the buffer can be used. The pH at which the solution is buffered can also be adjusted by adjusting the molar ratio of the imidazole and hydrochloric acid used to form the salt.

The organic base forming the buffer may be present at a concentration from 0.03 $mol.dm^{-3}$ to 0.07 $mol.dm^{-3}$. Preferably from 0.045 mol.dm$^{-3}$ to 0.055 mol.dm$^{-3}$, and preferably about 0.05 mol.dm$^{-3}$.

A wetting agent may also be included in the phosphorus containing solution.

Additional plant nutrients, such as a source of nitrogen may also be added. The nutrient may comprise urea, ammonium nitrate, potassium nitrate, magnesium nitrate, and calcium nitrate. It will be appreciated that the nitrogen containing base such as imidazole may also serve as a source of nitrogen.

The phosphorus containing solution may be for treating plants. In one embodiment of the invention the phosphorus containing solution may be a fertiliser solution.

In another embodiment of the invention the phosphorus containing solution may comprise a fungicide. Preferably it comprises a fungicide suitable for use against Oomycetes, preferably for use against Peronosporales, preferably for use against Phytophthora and Pythium species.

According to another aspect of the present invention there is provided a method of preparing a buffered phosphorus containing solution comprising the step of mixing together:

- at least one phosphorus compound selected from the group consisting of phosphorous acid, hypophosphorous acid, polyphosphorous acid, polyhypophosphorous acid, and salts thereof;
- water; and
- an organic base in the form of a nitrogen containing compound and its conjugate acid to buffer the solution.

Preferably the phosphorus compound comprises a salt of phosphorous acid. The salt of phosphorous acid may be prepared by reacting phosphorous acid with a suitable base. Preferably the base is added in such an amount to provide the solution at a pH suitable for foliar uptake. Usually this is at a pH from about 5 to about 7. Preferably the pH is from about 6 to 7. Most preferably the pH is about 6.5. The salt may be prepared by first reacting phosphorous acid with a first base (such as potassium carbonate) and thereafter reacting it with another base (such as KOH). The first base may comprise a compound which does not include hydroxide, preferably it is a carbonate, and preferably it is an alkali metal carbonate. The other base may comprise a hydroxide containing compound, preferably an alkali metal hydroxide. The first base may be a weaker base than the second base. It is believed that the addition of a salt such as potassium carbonate increases the solubility of the phosphorous acid salt. The phosphorous acid may be reacted with the suitable base in the presence of water.

The invention also relates to the use of a phosphorus containing solution substantially as described hereinabove for treating plants or a locus especially a locus where plants are cultivated or to be cultivated. The solution may be used as a fungicide. Alternatively or additionally the solution may be used as a fertiliser. The solution may be applied directly to the plants, for example by spraying the plants or by drenching their roots, but preferably by applying it to the foliage of the plants. The solution may also be injected into plant, preferably into the stems, of plants.

The invention also relates to a method of treating a plant or a locus comprising applying to the plant or locus a phosphorus containing solution substantially as described hereinabove.

The invention will now be further described by means of the following non-limiting examples:

EXAMPLE 1

Preparation of Potassium Salt of Phosphorous Acid

Dry phosphorous acid (99% purity) in an amount of 563.89 kg was mixed with dry potassium carbonate (99.5% purity) in an amount of 360 kg. After mixing for about 15 minutes, 333 l of water was slowly added under stirring over a period of approximately 30 minutes. Potassium hydroxide (99% purity) in an amount of 200 kg was then added proportion-wise over a period of about 30 minutes.

Alternatively water in an amount of 330 l was placed in a container into which was added, with constant stirring, 110 kg phosphorous acid (99% purity) followed by 70 kg potassium carbonate (99.5% purity) followed by 40 kg potassium hydroxide. This was repeated four times after which 123.89 kg phosphorous acid was added followed by 80 kg potassium carbonate followed by 40 kg potassium hydroxide. According 563.89 kg phosphorous acid, 360 kg potassium carbonate and 200 kg potassium hydroxide was used.

A colorant in the form of Hexacol Acid Blue 9 in an amount of 10 g was then dissolved in 20 l of water and this solution was then added to the phosphorous acid solution. The colorant provides the solution with a light-blue colour to distinguish it from water.

EXAMPLE 2

Preparation of Buffered Solution

Imidazole (99% purity) in an amount of 3.44 kg was mixed with 30% aqueous hydrochloric acid (5.210 kg) and this mixture was added to the solution of example 1 to provide the buffered solution. The pH of the solution was 6.27 and the solution was stable.

EXAMPLE 3

Comparison of Buffer Capacity Between Imidazole Buffered Solution According to the Invention and Citric Acid Buffered Solution An amount of 100 ml of the imidazole buffered solution of example 2 was used. This buffer solution had a pH of 6.27 and a density of 1.4868 g. cm$^{-3}$.

A citric acid buffered solution of phosphorous acid was prepared as set out in example 6 of U.S. Pat. No. 5,514,200. The following compounds in the amounts indicated were mixed together:

| | |
|---|---|
| Phosphorous acid | 34,987 g |
| Citric acid (monohydrate) | 10,168 g |
| Potassium hydroxide | 39,807 g |

Water added to total volume of 100 ml.

The citric acid buffered solution had a pH of 5.71 and a density of 1.3749 g.cm$^{-3}$.

The above two buffered solutions were then diluted as follows:

- Solution (a): 10 ml of each undiluted buffer solution.
- Solution (b): 10 ml of each buffer solution diluted with 10 ml of distilled water (50% solution).
- Solution (c) : 10 ml of each buffer solution diluted with 40 ml of distilled water (20% solution).
- (d): Solution (d): 10 ml of each buffer solution diluted with 90 ml of distilled water (10% solution).

The diluted solutions were then titrated using a 1.0 M solution of sodium to determine their buffer capacities. Tables 1 and 2 provide the pH values obtained.

TABLE 1 pH of the solutions of Citric Buffer

| Ml of 1.0M NaOH solution added | Solution (a) | Solution (b) | Solution (c) | Solution (d) |
|---|---|---|---|---|
| 1 | 2.03 | | | |
| 2 | 2.06 | 2.12 | 2.16 | 2.11 |
| 3 | 2.09 | | | |
| 4 | 2.11 | 2.24 | 2.43 | 2.25 |
| 5 | 2.15 | | | |
| 6 | 2.18 | 2.39 | 2.70 | 2.41 |
| 8 | 2.28 | 2.70 | 3.12 | 2.64 |
| 10 | 2.38 | 3.03 | 3.56 | 2.92 |
| 12 | 2.48 | 3.43 | 3.96 | 3.29 |
| 14 | 2.61 | 3.89 | 4.35 | 3.77 |
| 16 | 2.74 | 4.27 | 4.66 | 4.18 |
| 18 | 2.88 | 4.58 | 4.90 | 4.56 |
| 20 | 3.06 | 4.84 | 5.10 | 4.85 |
| 22 | 3.27 | 5.04 | 5.25 | 5.05 |
| 24 | 3.48 | 5.21 | 5.38 | 5.24 |
| 26 | 3.73 | 5.36 | 5.51 | 5.40 |
| 28 | 3.93 | 5.48 | 5.62 | 5.54 |
| 30 | 4.13 | 5.59 | 5.72 | 5.61 |
| 32 | 4.33 | 5.70 | 5.82 | |
| 34 | 4.50 | | 5.91 | |
| 35 | | 5.84 | | 5.90 |
| 36 | 4.67 | | 6.00 | |
| 38 | 4.80 | | 6.08 | |
| 40 | 4.93 | 6.08 | 6.17 | 6.12 |
| 42 | 5.04 | | | |
| 44 | 5.14 | | | |
| 45 | | 6.31 | 6.38 | 6.35 |
| 46 | 5.24 | | | |
| 48 | 5.31 | | | |
| 50 | 5.40 | 6.55 | 6.62 | 6.54 |
| 52 | 5.51 | 6.66 | | |
| 54 | 5.58 | 6.77 | | |
| 55 | | | 6.95 | 6.80 |
| 56 | 5.64 | 6.89 | | |
| 58 | 5.70 | 7.04 | | |
| 60 | 5.76 | 7.23 | 7.62 | 7.13 |
| 62 | | 7.47 | 10.86 | |
| 63 | | 7.69 | 11.88 | |
| 64 | | 8.00 | 12.17 | |
| 65 | 5.90 | 9.50 | 12.34 | 7.78 |
| 66 | | 11.98 | 12.46 | |
| 67 | | 12.30 | | |
| 68 | | 12.48 | 12.62 | |
| 70 | 6.02 | 12.70 | 12.71 | 12.16 |
| 72 | | | | 12.44 |
| 74 | | | | 12.58 |
| 75 | 6.14 | 12.97 | | |
| 76 | | | | 12.66 |
| 80 | 6.26 | 13.11 | | 12.80 |
| 85 | 6.37 | | | 12.93 |
| 90 | 6.48 | | | 13.02 |
| 95 | 6.59 | | | |
| 100 | 6.72 | | | |
| 105 | 6.96 | | | |
| 110 | 7.35 | | | |
| 112 | 7.52 | | | |
| 114 | 8.46 | | | |
| 116 | 11.95 | | | |
| 118 | 12.41 | | | |
| 120 | 12.59 | | | |
| 125 | 12.83 | | | |

TABLE 2 pH of the solutions of Imidazole Buffer

| Ml of 1.0M NaOH solution added | Solution (a) | Solution (b) | Solution (c) | Solution (d) |
|---|---|---|---|---|
| 2 | 2.06 | 2.06 | 2.06 | 2.08 |
| 4 | 2.16 | 2.12 | 2.14 | 2.17 |
| 6 | 2.28 | 2.19 | 2.25 | 2.28 |
| 8 | 2.45 | 2.30 | 2.38 | 2.45 |
| 10 | 2.72 | 2.41 | 2.56 | 2.68 |
| 12 | 3.42 | 2.56 | 2.88 | 3.23 |
| 14 | 4.25 | 2.82 | 3.79 | 4.50 |
| 16 | 4.61 | 3.35 | 4.68 | 4.94 |
| 18 | 4.84 | 4.46 | 5.01 | 5.18 |
| 20 | 5.02 | 4.86 | 5.21 | 5.34 |
| 22 | 5.18 | 5.08 | 5.36 | 5.46 |
| 24 | 5.29 | 5.26 | | |
| 25 | | | 5.53 | 5.63 |
| 26 | 5.37 | 5.38 | | |
| 28 | 5.46 | 5.49 | | |
| 30 | 5.54 | 5.58 | 5.74 | 5.82 |
| 32 | 5.61 | | | |
| 34 | 5.69 | | | |
| 35 | | 5.79 | 5.92 | 6.00 |
| 36 | 5.76 | | | |
| 38 | 5.82 | | | |
| 40 | 5.87 | 5.96 | 6.08 | 6.14 |
| 45 | 6.01 | 6.12 | 6.22 | 6.28 |
| 50 | 6.15 | 6.28 | 6.35 | 6.42 |
| 52 | | | | 6.49 |
| 55 | 6.33 | 6.43 | 6.51 | 6.58 |
| 58 | | | | 6.68 |
| 60 | 6.49 | 6.57 | 6.66 | 6.74 |
| 63 | | | | 6.85 |
| 65 | 6.67 | 6.72 | 6.84 | 6.92 |
| 68 | | | | 7.04 |
| 70 | 6.89 | 6.89 | 7.06 | 7.13 |
| 72 | 7.02 | | | |
| 73 | | | | 7.31 |
| 75 | 7.23 | 7.14 | 7.32 | 7.46 |
| 78 | | | | 7.74 |
| 80 | 8.08 | 7.49 | 7.91 | 8.16 |
| 81 | 8.90 | | | |
| 82 | 11.56 | 7.70 | 8.70 | 11.13 |
| 83 | 12.02 | | | 11.95 |
| 84 | 12.24 | 8.19 | 12.05 | 12.27 |
| 85 | 12.37 | | | 12.43 |
| 86 | | 11.64 | 12.47 | |
| 88 | | 12.33 | 12.67 | |
| 90 | 12.70 | 12.56 | 12.79 | 12.81 |
| 92 | | 12.71 | | |
| 94 | | 12.77 | | |
| 95 | | | 13.00 | 13.00 |
| 96 | | 12.87 | | |
| 100 | | 12.99 | 13.11 | 13.10 |

From the results obtained it can be seen that both buffering systems buffered the solution at a pH between approximately 5 and 7. It can be seen that when considering the undiluted solution (a) of the citric acid buffer and imidazole buffer, that the citric acid buffer was twice as effective at neutralising the NaOH additions. The buffering effect of the concentrated solutions is not important in practise since the solutions will always be diluted, accordingly this result is of minimal importance. The results of the diluted solutions are more important as the solutions will be used in dilute solutions. In the dilute solutions it can be seen that the citric acid throughout could only neutralise 0.04 moles of NaOH while buffering the solution between pH 5–7, the imidazole buffer on the other hand was able to neutralise 0.055 moles of NaOH while buffering the solution between the same pH range. It can be seen with the help of these titrations that the imidazole buffer can neutralise approximately 30% more NaOH than the citric acid buffer. This translates into a 30% improvement of the buffering ability of the solution.

The buffered phosphorus containing solution of example 2 may be used for treating plants or a locus where plants are cultivated or to be cultivated. The solution may be used as a fertiliser. Alternatively or additionally it may be used to treat plant diseases such as fungus.

When used as a fungicide or fertiliser the solution is preferably diluted.

When used as a fertiliser or fungicide the solution may be diluted to contain from 0.2 mol.dm$^{-3}$ or less of the phosphorus compound, preferably from 0.1 mol.dm$^{-3}$ or less and preferably about 0.02 mol.dm$^{-3}$.

When used as a fertiliser or fungicide the solution may be applied at a rate from 0.5 mol/hectare to 600 mol/hectare, preferably from 2.4 mol/hectare to 360 mol/hectare and preferably about 40 mol/hectare of the phosphorus compound.

It will be appreciated that concentration and application rates depend on many factors such as the type of crop, conditions and application methods.

It will be appreciated that many variations in detail are possible without thereby departing from the scope and spirit of the invention.

What is claimed is:

1. A buffered phosphorus solution comprising: at least one phosphorus compound selected from the group consisting of phosphorous acid, hypophosphorous acid, polyphosphorous acid, polyhypophosphorous acid, and salts thereof; and a buffer including an organic base in the form of an imidazole and its conjugate acid, which buffer buffers the solution at a pH suitable for foliar uptake.

2. The solution according to claim 1 which is a concentrated solution containing from 2 mol.dm$^{-3}$ to 8 mol.dm$^{-3}$ of the phosphorus compound.

3. The solution according to claim 1 wherein the phosphorus compound comprises phosphorous acid and/or a salt thereof.

4. The solution according to claim 3 wherein the phosphorus compound comprises an alkali metal salt or an alkaline earth metal salt of phosphorous acid.

5. The solution according to claim 4 wherein the phosphorus compound comprises a potassium salt of phosphorous acid.

6. The solution according to claim 5 which comprises a mixture of $KH_2PO_3$ and $K_2HPO_3$.

7. The solution according to claim 4 wherein the salt is the reaction product of phosphorous acid with a first base and another base, the first base comprising a compound which does not include hydroxide and the other base comprising a hydroxide containing compound.

8. The solution according to claim 7 wherein the first base comprises an alkali metal carbonate and the other base comprises an alkali metal hydroxide.

9. The solution according to claim 1 wherein the buffer is the reaction product of imidazole and a mineral acid.

10. The solution according to claim 9 wherein the mineral acid comprises hydrochloric acid.

11. The solution according to claim 10 which buffers the solution at a pH from about 5 to about 7.

12. The solution according to claim 2 in which the phosphorus compound comprises a mixture of $KH_2PO_3$ and $K_2HPO_3$ and the buffer is a reaction product of imidazole and a mineral acid.

13. The solution according to claim 12 which is buffered at a pH of from about 5 to about 7.

14. A solution according to claim 1 which is a fertiliser solution.

15. A solution according to claim 1 which is a fungicidal solution.

16. A method of preparing a buffered phosphorus containing solution comprising the step of mixing together:
    at least one phosphorus compound selected from the group consisting of phosphorous acid, hypophosphorous acid, polyphosphorous acid, polyhypophosphorous acid, and salts thereof;
    water; and
    an organic base in the form of an imidazole and its conjugate acid to buffer the solution.

17. The method according to claim 16 wherein the phosphorus compound comprises a salt of phosphorous acid, said salt being prepared by first reacting the phosphorous acid with a first base and thereafter reacting it with another base.

18. The method according to claim 17 wherein the first base comprises a compound which does not include hydroxide and the other base comprises a hydroxide containing compound.

19. The method according to claim 18 wherein the first base comprises an alkali metal carbonate and the second base comprises an alkali metal hydroxide.

* * * * *